US006465379B1

(12) United States Patent
Cook et al.

(10) Patent No.: US 6,465,379 B1
(45) Date of Patent: Oct. 15, 2002

(54) UNITARY ABSORBENT MATERIAL FOR USE IN ABSORBENT STRUCTURES

(75) Inventors: Jeffery T. Cook, Germantown, TN (US); Howard L. Schoggen, Southaven, MS (US)

(73) Assignee: BKI Holding Corporation, Wilmington, DE (US)

( * ) Notice: Subject to any disclaimer, the term of this patent is extended or adjusted under 35 U.S.C. 154(b) by 0 days.

(21) Appl. No.: 09/343,055

(22) Filed: Jun. 29, 1999

Related U.S. Application Data

(60) Provisional application No. 60/091,279, filed on Jun. 30, 1998.

(51) Int. Cl.[7] .......................... B32B 5/16; B32B 27/04; B32B 21/02

(52) U.S. Cl. ....................... 442/393; 442/118; 442/385; 442/417

(58) Field of Search .................. 604/368; 442/381, 442/385, 393, 417, 118

(56) References Cited

U.S. PATENT DOCUMENTS

| 3,545,441 A | 12/1970 | Gravdahl ..................... 128/284 |
| 3,769,115 A | 10/1973 | Rasmussen et al. ........ 156/62.2 |
| 3,871,378 A | 3/1975 | Ducan et al. ................ 128/290 |
| 3,938,522 A | 2/1976 | Repke .......................... 128/287 |
| 3,965,904 A | 6/1976 | Mesek et al. ................. 128/284 |
| 4,011,034 A | 3/1977 | Curry et al. ................... 425/80 |
| 4,044,768 A | 8/1977 | Mesek et al. ................. 128/287 |
| 4,045,833 A | 9/1977 | Mesek et al. ..................... 5/335 |
| 4,074,721 A | 2/1978 | Smits et al. .................. 128/461 |
| 4,081,316 A | 3/1978 | Aberg et al. ..................... 162/4 |
| 4,102,340 A | 7/1978 | Mesek et al. ................. 128/287 |
| 4,103,062 A | 7/1978 | Aberson et al. ............. 428/283 |
| 4,145,464 A | 3/1979 | McConnell et al. ......... 428/172 |
| 4,217,901 A | 8/1980 | Bradstreet et al. .......... 128/290 |
| 4,256,111 A | 3/1981 | Lassen ......................... 128/284 |
| 4,259,387 A | 3/1981 | Mesek .......................... 428/167 |
| 4,276,338 A | 6/1981 | Ludwa et al. ................ 428/137 |
| 4,333,463 A | 6/1982 | Holtman ...................... 128/287 |
| 4,364,992 A | 12/1982 | Ito et al. ...................... 428/283 |
| 4,397,644 A | 8/1983 | Matthews et al. ........... 604/378 |
| 4,578,070 A | 3/1986 | Holtman ...................... 604/378 |
| 4,600,458 A | 7/1986 | Kramer et al. ............... 156/199 |
| 4,670,011 A | 6/1987 | Mesek .......................... 604/378 |
| 4,673,402 A | 6/1987 | Weisman et al. ............ 604/368 |
| 4,699,619 A | 10/1987 | Bernardin .................... 604/378 |
| 4,699,620 A | 10/1987 | Bernardin .................... 604/385 |
| 4,714,466 A | 12/1987 | Dohzono et al. ............ 604/378 |
| 4,755,178 A | 7/1988 | Insley et al. ................. 604/367 |
| 4,806,408 A | 2/1989 | Pierre et al. ................... 428/76 |
| 4,822,453 A | 4/1989 | Dean et al. ............... 162/157.6 |
| 4,826,498 A | 5/1989 | Koczab ........................ 604/383 |
| 4,834,735 A | 5/1989 | Alemany et al. ............ 604/368 |
| 4,857,065 A | 8/1989 | Seal ............................. 604/368 |
| 4,885,204 A | 12/1989 | Bither et al. ................. 428/284 |
| 4,888,231 A | 12/1989 | Angstadt ..................... 428/213 |
| 4,935,022 A | 6/1990 | Lash et al. ................... 604/368 |
| 4,941,948 A | 7/1990 | Yamamoto ................... 162/142 |
| 4,980,226 A | 12/1990 | Hellgren et al. ............. 428/218 |
| 4,988,344 A | 1/1991 | Reising et al. ............... 604/368 |
| 4,994,037 A | 2/1991 | Berardin ...................... 604/368 |
| 5,009,650 A | 4/1991 | Bernardin .................... 604/378 |

(List continued on next page.)

Primary Examiner—Terrel Morris
Assistant Examiner—Christopher C. Pratt
(74) Attorney, Agent, or Firm—Darby & Darby

(57) ABSTRACT

A layered composite suitable for disintegration into superabsorbent cellulose fluff suitable for use as a core material in an absorbent product. The composite includes a wetlaid web of cellulosic fibers; a layer of superabsorber disposed on the wetlaid web; a drylaid cellulosic layer disposed on the superabsorber layer; wherein the layer of superabsorbent particles comprises greater than 50 percent by weight of the composite; and the drylaid cellulosic layer does not include a bonding agent.

10 Claims, 3 Drawing Sheets

U.S. PATENT DOCUMENTS

| | | | |
|---|---|---|---|
| 5,019,063 A | 5/1991 | Marsan et al. | 604/368 |
| 5,041,104 A | 8/1991 | Seal | 604/367 |
| 5,043,206 A | 8/1991 | Ternstrom | 428/218 |
| 5,069,676 A | 12/1991 | Ito et al. | 604/358 |
| 5,079,074 A | 1/1992 | Steagall et al. | 428/218 |
| 5,128,193 A | 7/1992 | Anapol et al. | 428/171 |
| 5,137,537 A | 8/1992 | Herron et al. | 8/120 |
| 5,183,707 A | 2/1993 | Herron et al. | 428/364 |
| 5,190,563 A | 3/1993 | Herron et al. | 8/120 |
| 5,217,445 A | 6/1993 | Young et al. | 604/381 |
| 5,219,341 A | 6/1993 | Serbiak et al. | 604/361 |
| 5,221,573 A | 6/1993 | Baigas, Jr. | 428/281 |
| 5,236,427 A | 8/1993 | Hamajima et al. | 604/378 |
| 5,246,429 A | 9/1993 | Poccia et al. | 604/368 |
| 5,262,005 A | 11/1993 | Eriksson et al. | 162/100 |
| 5,271,987 A | 12/1993 | Iskra | 428/192 |
| 5,281,207 A | 1/1994 | Chmielewski | 604/377 |
| 5,294,478 A | 3/1994 | Wanek et al. | 428/218 |
| 5,300,054 A | 4/1994 | Feist et al. | 604/378 |
| 5,304,161 A | 4/1994 | Noel et al. | 604/378 |
| 5,348,547 A | 9/1994 | Payne et al. | 604/378 |
| 5,354,427 A | 10/1994 | Rasmussen | 162/218 |
| 5,356,403 A | 10/1994 | Faulks et al. | 604/378 |
| 5,356,405 A | 10/1994 | Thompson et al. | 604/384 |
| 5,360,420 A | 11/1994 | Cook et al. | 604/378 |
| 5,366,451 A | 11/1994 | Leveaque | 604/378 |
| 5,374,260 A | 12/1994 | Lemay et al. | 604/378 |
| 5,384,179 A | 1/1995 | Roe et al. | 428/192 |
| 5,387,208 A | 2/1995 | Ashton et al. | 604/378 |
| 5,391,161 A | 2/1995 | Hellgren et al. | 604/366 |
| 5,415,736 A | 5/1995 | Grether | 162/111 |
| 5,419,956 A | 5/1995 | Roe | 428/283 |
| 5,458,591 A | 10/1995 | Roessler et al. | 604/364 |
| 5,460,622 A | 10/1995 | Dragoo et al. | 604/378 |
| 5,466,232 A | 11/1995 | Cadieux et al. | 604/378 |
| 5,466,513 A | 11/1995 | Wanek et al. | 428/218 |
| 5,470,326 A | 11/1995 | Dabi et al. | 604/383 |
| 5,476,459 A | 12/1995 | Yang | 604/385.1 |
| 5,484,429 A | 1/1996 | Vukos et al. | 604/385.1 |
| 5,484,896 A | 1/1996 | Naieni et al. | 530/504 |
| 5,486,167 A | 1/1996 | Dragoo et al. | 604/384 |
| 5,505,719 A | 4/1996 | Cohen et al. | 604/372 |
| 5,525,407 A | 6/1996 | Yang | 428/218 |
| 5,531,728 A | 7/1996 | Lash | 604/378 |
| 5,536,264 A | 7/1996 | Hsueh et al. | 604/368 |
| 5,536,369 A | 7/1996 | Norlander | 162/157.6 |
| 5,549,589 A | 8/1996 | Horney et al. | 604/366 |
| 5,558,655 A | 9/1996 | Jezzi et al. | 604/378 |
| 5,599,335 A | 2/1997 | Goldman et al. | 604/368 |
| 5,599,336 A | 2/1997 | Plischke | 604/368 |
| 5,601,542 A | 2/1997 | Melius et al. | 604/368 |
| 5,643,238 A | 7/1997 | Baker | 604/368 |
| 5,643,240 A | 7/1997 | Jackson et al. | 604/378 |
| 5,649,916 A | 7/1997 | DiPalma et al. | 604/378 |
| 5,669,894 A | 9/1997 | Goldman et al. | 604/368 |
| 5,695,846 A | 12/1997 | Lange et al. | 428/98 |
| 5,728,081 A | 3/1998 | Baer et al. | 604/370 |
| 5,762,641 A | 6/1998 | Bewick-Sonntag et al. | 604/378 |
| 5,763,067 A | 6/1998 | Bruggemann et al. | 428/317.9 |
| 5,763,331 A | 6/1998 | Demhartner | 442/68 |
| 5,785,696 A | 7/1998 | Inoue et al. | 604/378 |
| 5,989,688 A * | 11/1999 | Barge et al. | 428/198 |

\* cited by examiner

UNITARY ABSORBENT MATERIAL FOR USE IN ABSORBENT STRUCTURES

RELATED APPLICATIONS

This application claims the benefit of U.S. Provisional Patent Application No. 60/091,279, filed Jun. 30, 1998.

FIELD OF THE INVENTION

The present invention relates to a multilayered, high density cellulose and superabsorber composite material useful for the preparation of superabsorbent cellulose fluff suitable for use in disposable absorbent articles such as infant diapers, feminine hygiene pads and adult incontinence pads.

BACKGROUND OF THE INVENTION

Recently, the demand for thinner and more comfortable absorbent articles, such as infant diapers, feminine hygiene pads, adult incontinence pads, and the like, has increased. The materials which are most widely used for the absorbent core of such absorbent articles are cellulose fibers and superabsorbent polymers. Superabsorbent polymers (hereinafter "superabsorbers") developed recently are capable of absorbing many times their own weight of liquid. Superabsorbers have been used to increase the absorbency of absorbent products such as infant diapers, feminine hygiene pads and adult incontinence pads.

When manufacturing absorbent cores, cellulose fibers, generated e.g., by hammermilling a cellulose pulp board, and superabsorbent polymers are typically introduced into the core by introducing them separately into the pad forming unit of a converting machine. The superabsorbent polymers are often provided in the form of granules, powders or fibers. Superabsorbent particles are well-known in the art and are described, e.g., in U.S. Pat. Re. 32,649 and U.S. Pat. No. 4,102,340. One art-recognized problem with introducing the cellulose and superabsorber into the absorbent core as separate materials is the difficulty in handling the superabsorber. Separately added superabsorber creates dust, which complicates maintenance and reduces the efficiency of the absorbent product pad converting machine. Further, superabsorber can attach to the outside of the absorbent products and cause product quality issues with the consumer because of its grittiness and hygroscopicity. Superabsorber dust and free particle production also results in superabsorber waste and attendant economic inefficiency.

Most methods to contain the superabsorber particles in absorbent fluff are directed at the machine design of the converter. A method for immobilization of superabsorber is disclosed in U.S. Pat. No. 4,444,830, where an absorbent polymer solution is coated on base fluffing material to form a film, and the coated fluffing material is dried, disintegrated and mechanically worked into a fibrous fluff matrix which contains absorbent polymer platelets distributed throughout the matrix. Fluff produced from such superabsorbent film composite materials have reduced absorbent capacity relative to fluff containing superabsorber in particulate form, because of a "gel blocking" phenomenon. Gel blocking occurs in fluff made from base fluffing materials coated with superabsorber film because the superabsorber film (as opposed to particles) has a very low permeability. As a result, fluid to be absorbed does not have access to the full absorbent core produced by disintegrating the superabsorber film-coated base fluffing material. The interaction of the fluid and the film platelets causes the superabsorber to swell in localized regions of the core. The fluid is then blocked by the superabsorber gel that is locally formed, and liquid pooling, as opposed to absorption, occurs in the core. This results in large portions of the core being unused, and of failure of the absorbent core.

U.S. Pat. No. 4,424,247 discloses composite laminates made of superabsorber bonded to a wicking substrate, where the superabsorber and the substrate are present in a 1:1 ratio. The laminates can be disintegrated into an absorbent fluff material suitable for use as an absorbent core. The resulting core material, however, has low levels of superabsorber. EP 359 615 discloses a superabsorbent fiber structure comprising absorbent cellulose fibers and solid absorbent particles formed by laying a preformed web over the absorbent. The resulting density of this structure must be low in order to prevent crushing of the superabsorber, which results in unsatisfactory absorbency properties. The structure described by EP 359 615 is disclosed to be useful as an absorbent core per se, as opposed to being useful as a material for subsequent disintegration, e.g. by hammermilling, in the preparation of an absorbent fluff core material.

The current state of the art is such that absorbent cores for such absorbent articles are produced with about 40 to 50% by weight superabsorber. It would be advantageous to increase the level of superabsorber in absorbent cores to 70% by weight or greater. Prior to the present invention, the art had not provided a way to satisfactorily achieve this superabsorber content in absorbent cores. Addition of such high levels of superabsorber with fluffed cellulose by mixing results in settling and separation of superabsorber away from the cellulose fibers of the absorbent core fluff. Compositions in which the base cellulosic fluffing material is bonded to superabsorber, and which are subsequently disintegrated, such as in U.S. Pat. Nos. 4,444,830 and 4,424,247, do not provide the ability to include superabsorbers at greater than 50 weight percent, and further are not dense enough to be economical to ship. The art recognizes that a finished composite base fluffing/superabsorber material should have a density of greater than about 0.40 grams per cubic centimeter to allow economical shipping and distribution.

It has now been surprisingly and unexpectedly discovered by the present inventors that a composite comprising a cellulosic base fluffing material and one or more superabsorbers can be produced that comprises greater than 50% superabsorber by weight, and which is suitable for disintegration into an absorbent core material, in which the superabsorber is closely associated with or entrapped between the cellulose fluff fibers. The composite of the invention is a high density material suitable for economical transport and storage.

SUMMARY OF THE INVENTION

In one aspect, the invention relates to a three layered high density composite material comprising a layer of wetlaid cellulose, a layer of drylaid (also known as "airlaid") cellulose and a layer of superabsorber disposed therebetween. The composite comprises greater than 50% by weight, and preferably greater than 70% by weight of superabsorber. The drylaid cellulose layer does not include an additional bonding agent, such as latex.

In one aspect, the layer of superabsorber is in direct contact with the wetlaid web of cellulosic fibers and the drylaid cellulosic layer is in direct contact with the superabsorber layer.

In another aspect, the invention relates to a method for producing a high density composite material suitable for disintegration into a superabsorbent fluff core material. The method comprises providing a wetlaid sheet, adding water, distributing a superabsorber layer onto the wetlaid sheet, and then providing a drylaid cellulose layer disposed adjacent to the superabsorber layer which entraps and immobilizes the superabsorber layer. The resulting three layer sheet is then lightly compressed.

In yet another aspect, the invention relates to a superabsorbent fluff material suitable for use as an absorbent core material in an absorbent article, including the superabsorber-associated fibers produced by the mechanical disintegration of the layered high density composite material of the invention.

In a further aspect, the invention relates to an absorbent article which includes the superabsorbent fluff material of the invention, and to methods for making such absorbent articles.

DETAILED DESCRIPTION OF THE INVENTION

Figure 1:
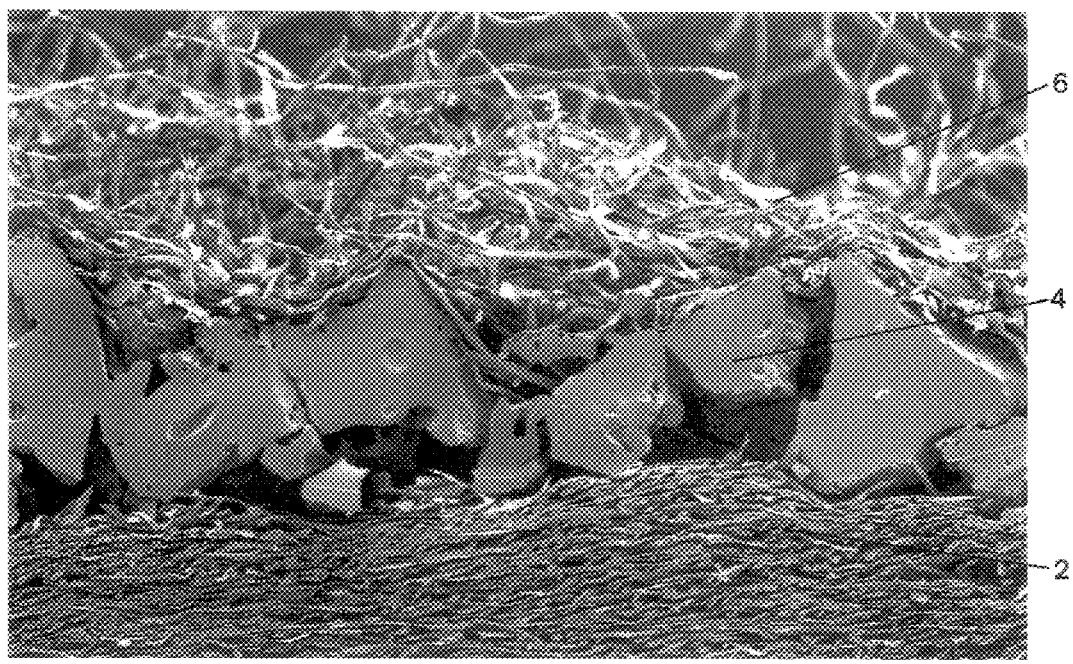
FIG. 1 is a photomicrograph of an embodiment of the three layer high density composite material of the invention.

All patents, patent applications, and publications cited in this specification are hereby incorporated by reference in their entirety. In case of a conflict in terminology, the present disclosure controls.

The high density three layered absorbent composite material of the invention comprises a fiber web of low density wetlaid cellulose, a dense layer of superabsorber, and a low density layer drylaid cellulose. The final density of the layered composite material of the invention ranges from about 0.30 grams per cubic centimeter to about 0.80 grams per cubic centimeter, preferably between about 0.40 grams per cubic centimeter and about 0.60 grams per cubic centimeter, most preferably about 0.52 grams per cubic centimeter.

As used herein, the term "wetlaid cellulose" means a sheet or mat of cellulose fibers formed from a slurry, usually an aqueous slurry, of cellulose fibers. Typically, the slurry is deposited on a fine wire mesh. The fiber sheet is then dried. Methods for the production of wetlaid cellulose layers of various densities are known in the art, and typically used in the pulp and paper industry.

As used herein, "drylaid cellulose" means a layer of fibers which is deposited on a wire mesh from a source such as a deposition chute or forming head. The fibers are produced, e.g., by hammermilling a cellulose sheet, suspending the disintegrated cellulose fibers in air, and depositing the fibers at very low density on a wire mesh. The term "drylaid" is synonomous with "airlaid".

As used herein, "superabsorber" means any of the known hydrophilic polymers that can be constructed in a composite of polymeric absorbent and fibrous adsorbents. A superabsorbent is a water soluble compound which has been cross-linked to render it water insoluble but still swellable to at least about 15 times its own weight in physiological saline solution. These superabsorbent materials generally fall into 3 classes, namely starch graft copolymers, crosslinked carboxymethylcellulose derivatives and modified hydrophilic polyacrylates. Non-limiting examples of such absorbent polymers are hydrolyzed starch-acrylonitrile graft co-polymer, a saponified acrylic acid ester-vinyl acetate co-polymer, a modified crosslinked polyvinyl alcohol, a neutralized crosslinked polyacrylic acid, a crosslinked polyacrylate salt, and carboxylated cellulose. The preferred superabsorbent materials, upon absorbing fluids, form hydrogels.

Such polymer materials have relatively high gel volume and relatively high gel strength as measured by the shear modulus of the hydrogel. Such preferred materials also contain relatively low levels of polymeric materials which can be extracted by contact with synthetic urine. Superabsorbent polymers are well-known and are commercially available, for example a starch graft polyacrylate hydrogel marketed under the name IM 1000 (Hoechst-Celanese, Portsmouth, Va.). Other commercially available superabsorbers are marketed under the trademark Sanwet (Sanyo Kasei Kogyo Kabushiki Kaishi, Japan), Sumika Gel (Sumitomo Kagaku Kabushiki Kaishi, Japan), Favor (Stockhausen, Grayville, La.), Norsocryl (Atochem, France) and the ASAP series of superabsorbers (Chemdal, Aberdeen, Miss.). Similar superabsorbers are available from BASF (Germany), Dow Chemical (Midland, Mich.) and NA Industries (Chattanooga, Tenn.). Superabsorbent particulate hydrophilic polymers are also described in detail in U.S. Pat. Nos. 4,102,340 and Re 32,649, which are incorporated herein by reference in their entirety. Any superabsorber may be used in the invention.

The high density three layer sheet that can be disintegrated in conventional hammer mills is shown in microscopic detail in FIG. 1 and is comprised of a wetlaid cellulose layer 2, a superabsorber layer 4, and a drylaid cellulose layer 6.

The density of drylaid cellulose layer 6 ranges from about 0.012 to about 0.018 grams per cubic centimeter (g/cc). Maintaining the density of drylaid cellulose layer 6 within this range is important because the low density of drylaid cellulose layer 6 allows the cellulose fibers of drylaid cellulose layer 6 to completely fill the gaps between the superabsorbent particles of superabsorber layer 4. The "filling in" function of the drylaid cellulose layer 6 allows the inclusion of very high weight percentages, i.e, greater than 70 weight percent, of superabsorber to be fully contained within the high density three layer sheet because of the high void volume in the low density layer. Drylaid cellulose layer 6 is formed by disintegrating a fluff sheet in a hammermill and dispersing the fibers onto the wetlaid layer and SAP layer. The hammermill used can be, e.g., a Kamas Cell Mill. Other types of hammermills suitable for disintegrating pulp to form drylaid cellulose layer 6 are well known in the art. In this embodiment the wetlaid sheet is manufactured as the bottom layer of the composite, the SAP is disposed as the middle layer, and the airlaid layer is the last "top" layer added in the process. In another embodiment, the process can be reversed, in that the airlaid fibers can be deposited onto a moving screen, followed by metering of high levels of SAP onto the airlaid layer, followed by unrolling of the wetlaid sheet onto the airlaid and SAP layers.

Water is also applied to the wetlaid cellulose layer 2 to aid the adherence of superabsorber layer 4 to the cellulose fibers of wetlaid cellulose layer 2 and drylaid cellulose layer 6.

Water is added to the wetlaid sheet in an amount in the range from about 15 to about 20% by weight of the wetlaid sheet. That is, e.g., for every 100 grams of wetlaid cellulose layer 2, about 20 ml of water is applied. The application of water causes the superabsorbent particles to swell slightly. Water is typically added by spraying a misted stream onto both the airlaid layer and the wetlaid layer at a flow rate sufficient to achieve a 15 to 20 percent moisture content by total weight of the composite.

The amount of superabsorbent polymer in the three layer sheet can be from 20 to greater than 70 weight percent, after drying of the sheet, preferably greater than about 50 weight percent, most preferably about 70 weight percent or greater.

The density of wetlaid cellulose layer 2 preferably ranges between about 0.20 to about 0.3 grams per cubic centimeter. This density range is important to maintain, because the low density of wetlaid cellulose layer 2 relative to a typical cellulose sheet, which typically has a density of 0.5 grams per cubic centimeter allows the superabsorbent particles of superabsorber layer 4 to be slightly pressed into the sheet, thereby increasing their level of immobilization which prevents dusting and loss of superabsorber during packaging, shipping, and disintegration into fluff. The wetlaid cellulose layer 2 is maintained at low density by not pressing the sheet early in the process to remove water, as is typically done with standard cellulose base fluffing materials. Water is removed by heat and air drying of the sheet.

In the process of preparing the three layer sheet of the invention, compression of the layers together is performed at very low pressures, ranging from about 60 to about 100 pounds per linear inch of three layer sheet. Compression at low pressures, which still yields a three layer structure that will not delaminate, is possible because of the low density of drylaid cellulose layer 6 and the slightly swollen and tacky superabsorbent particles of superabsorber layer 4. Compression of the three layer sheet can be performed with calendaring machines which are well-known in the art. The compression machine can provide low pressure ranging from about 60 to about 100 pounds per linear inch. The layered structure is inserted between moving calendar rolls and compressed. Any compression machine would work adequately.

Low pressure compression is not be possible if drylaid cellulose layer 6 contains bonding agents such as, e.g., latex. This is because the presence of the bonding agent would increase the density of drylaid layer 6 to a level that would require high pressure to achieve bonding with the superabsorber layer 4 and wetlaid cellulose layer 2. Excess pressure results in damage to the superabsorbent particles of superabsorber layer 4. Typically such damage is crushing, which yields superabsorber particles with a sub-optimal size distribution, which can result in gel-blocking in the finished absorbent product. Gel blocking occurs when superabsorber particles are too small or too thin, resulting in a sub-optimal surface to volume ration, i.e., the ratio is too high. These particles interact too quickly with fluid, thereby becoming saturated too quickly, which creates a gel that does not allow the excess fluid to wick to other regions of the structure. Further, addition of a bonding agent, such as latex, to drylaid layer 6 would impede disintegration of the composite sheet of the invention into superabsorbent fluff, thereby decreasing or eliminating the utility of the composite sheet of the invention as a precursor material for superabsorbent fluff. Accordingly, drylaid cellulose layer 6 does not contain a bonding agent.

The three layered composite material can be disintegrated using the various types of hammermill disintegrators or refiners which are well-known in the art. One example is the Kamas Cell Mill. The three layer composite material is introduced into the device just as a typical pulp sheet would be introduced. The composite is disintegrated and the fibers and accompanying superabsorber are laid onto a forming drum or web. The final shape and thickness of the absorbent core produced by disintegration of the three layered composite of the invention can be tailored to the specific product design of the diaper, feminine hygiene or adult incontinence product for which the core is intended.

Thus, in accordance with the present invention, absorbent structures or articles may be made from the superabsorbent cellulose fluff made with the three layered composite material of the invention. These products are capable of absorbing significant quantities of water and other fluids, such as urine and other body fluids. Such products include, but are not limited to, disposable diapers, feminine hygiene products, adult incontinence products, towels, and the like.

The following Examples are intended to illustrate the invention without limitation.

EXAMPLE 1

A wetlaid sheet was produced at 0.25 grams per cubic centimeter density and a basis weight of 175 grams per square meter (gsm) by weighing out 37.5 grams of sheeted Buckeye Foley Fluff, which was run through a Tappi disintegrator (British Pulp Evaluation Apparatus, Mavis Engineering Ltd. of London, England) for 5 minutes. The disintegrated material was then transferred to a dynamic handsheet former, (Center Technique De L'Industrie—Des Papiers Cartons & Celluloses, France) using a 25/10 nozzle and 1.5 bar pressure. The former was set to produce a sheet with a density of 175 grams per square meter,, and a wetlaid sheet of pulp of this density was laid down. The wetlaid sheet is dried to zero percent moisture in a drum dryer (Buckeye Technologies Inc., Memphis, Tenn.). The sheet was then cut into a 4"×14" sample, and conditioned with standard Tappi temperature and humidity of 70 ° F. and 50% humidity for 24 hours. Seventeen percent moisture was added to the sheet by spraying 0.29 gram of water per gram to the wetlaid layer. Superabsorbent particles were added at 680 grams per square meter to the wetlaid sheet by metering the measured amount onto a sheet. Dry fibers were laid onto the superabsorbent particles to form a drylaid cellulose layer. The dry fibers were made by disintegrating a cellulose fluff sheet introduced into a hammermill at 11 feet per minute, using a 2 inch Kamas Cell Mill from Kamas Industri AB, Sweden, and then forming the layer such that the weight of the drylaid layer was 113 grams per square meter. The cellulose fluff sheet was Buckeye Foley Fluff available from Buckeye Technologies, Memphis, Tenn. The hammermill rotated at 5000 RPM. No screen was used. The loose fibers were collected and then introduced into a forming head (Buckeye Technologies Inc., Memphis, Tenn.). 0.14 gram of water per gram of drylaid layer was sprayed on the drylaid layer, to achieve 17% moisture. The layered structure was compressed with less than 100 pounds per linear inch pressure with a roll calendar machine (Buckeye Technologies, Inc., Memphis, Tenn.). The resulting weight ratio of superabsorber to cellulose fibers was 6 to 1. The density of the resulting product was 0.52 grams per cubic centimeter. The following table summarizes the parameters of the sheet produced.

| | |
|---|---|
| Total Basis Weight, gsm | 1000 |
| Total Density, grams per cubic centimeter | 0.52 |
| Superabsorbent content, % | 70 |
| Drylaid basis weight, gsm | 113 |
| Wetlaid basis weight, gsm | 175 |
| Ratio superabsorber to drylaid cellulose layer | 6 to 1 |

EXAMPLE 2

All procedures were conducted as in Example 1, unless otherwise noted. A wetlaid cellulose sheet was produced at 0.25 grams per cubic centimeter density and with a basis weight of 375 grams per square meter (gsm) using the procedure set forth in Example 1. The wetlaid sheet was dried to zero percent moisture, and then 17% moisture was added to the sheet. Superabsorbent particles were added at 1361 gsm of wetlaid sheet. Dry fibers were laid onto the superabsorbent particles such that the basis weight of the drylaid layer was 226 gsm. The layered structure was compressed. The weight ratio of superabsorber to drylaid cellulose layer is 6 to 1. The density of the multilayered sheet was 0.52 grams per cubic centimeter.

EXAMPLE 3

A wetlaid sheet was produced at 0.25 grams per cubic centimeter density and a basis weight 350 grams per square meter (gsm) using the procedure set out in Example 1. The wetlaid sheet was dried to zero percent moisture, and then 17% moisture was added to the sheet. Superabsorbent particles were added at 420 gsm of wetlaid sheet. Dry cellulose fibers were laid onto the superabsorbent particles such the weight of the resulting drylaid layer was 69 gsm. The layered structure was compressed. The weight ratio of superabsorber to drylaid cellulose is 6 to 1. The density of the resulting multilayered sheet was 0.49 grams per cubic centimeter.

EXAMPLE 4

The cellulose and superabsorbent material was made using the same procedure as Example 3. The resulting three layer material was disintegrated using the Kamas Cell Mill and laid into a homogeneously blended absorbent core. The material was then evaluated for retention of superabsorber on cellulose fibers by sifting the fibrous core through a series of screens. The amount of superabsorber, by weight, present on core material retained on the 20 mesh screen versus the control core material obtained from a commercially available absorbent product, was compared. The core of the control material is produced by simple mixing of disintegrated base fluffing material and superabsorber.

| | Weight % SAP in 20 Mesh Retained Core Material |
|---|---|
| Example 3 | 37.5 |
| Commercially obtained control | 19.1 |

Figure 2:
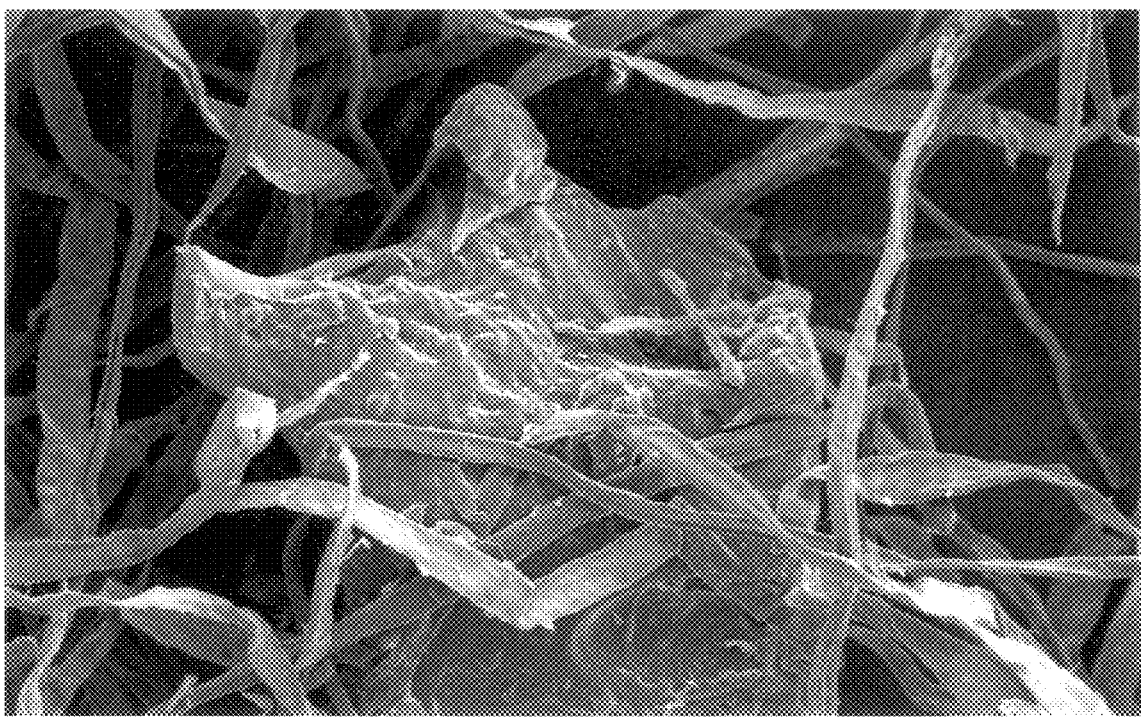
FIG. 2 is a photomicrograph of superabsorbent fluff produced by hammermilling the three layer high density composite material produced according to the present invention, illustrating the tight association between superabsorbent particles and cellulose fibers.
Figure 3:
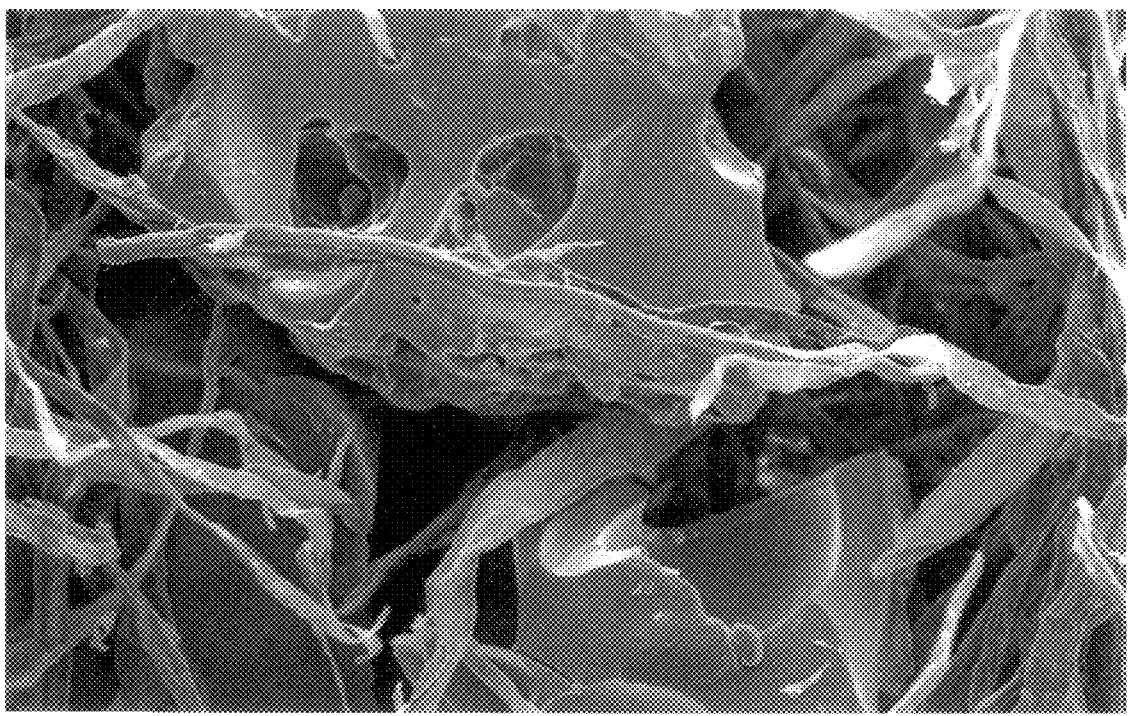
FIG. 3 is a photomicrograph of fluff and superabsorbent particles taken from a commercially available absorbent product, illustrating the loose association between cellulose fibers and superabsorbent particles.

Thus, absorbent fluff core materials produced by disintegration of the three layered composite material of the present invention contain a greater amount of superabsorber, by weight, than the core materials currently being used in absorbent products. FIGS. 2 and 3 also illustrate the greater association of superabsorber with cellulose fibers of core material made with the three layer composite of the present invention (FIG. 2), where it can be seen in a photomicrograph that the cellulose fibers are tightly associated with the superabsorbent particle. FIG. 3 shows the loose association of superabsorber particle with the cellulose fibers of the absorbent core material taken from the commercially available absorbent article.

These examples demonstrate that a high density composite material comprising very high levels of superabsorber can be produced, without damaging or decreasing the performance of the superabsorber material utilized in the composite. In addition, when disintegrated into fluff and used in an absorbent structure, the composite of the invention provides for increased superabsorber attachment to cellulose fibers in absorbent structures.

Many variations of the present invention will suggest themselves to those skilled in the art in light of the above detailed description. Such obvious variations are within the full intended scope of the appended claims.

What is claimed is:

1. A layered composite suitable for disintegration into superabsorbent cellulose fluff, consisting essentially of:
   a wetlaid web of cellulosic fibers;
   a layer of superabsorber in direct contact with said wetlaid web;
   a drylaid cellulosic layer in direct contact with said superabsorber layer; wherein
   said composite comprises greater than 50 percent by weight of said superabsorber; and
   said drylaid cellulosic layer does not include a bonding agent.

2. The layered composite of claim 1 wherein said superabsorber is in granular form.

3. The layered composite of claim 1 wherein said superabsorber is in powder form.

4. The layered composite of claim 1 wherein said superabsorber is in flaked form.

5. The layered composite of claim 1 wherein said superabsorber is in film form.

6. The layered composite of claim 1 wherein said superabsorber is in fiber form.

7. The layered composite of claim 1, wherein said layer of superabsorbent particles comprises greater than 70 percent by weight of said layered composite.

8. The layered composite of claim 1, wherein the density of said drylaid cellulosic layer ranges from about 0.012 to about 0.018 grams per cubic centimeter.

9. The layered composite of claim 1, wherein the density of said wetlaid cellulosic layer ranges from about 0.20 to about 0.27 grams per cubic centimeter.

10. The layered composite of claim 1, wherein said layered composite has a density ranging from about 0.4 to about 0.6 grams per cubic centimeter.

* * * * *